(12) United States Patent
Nesakumar et al.

(10) Patent No.: US 7,902,314 B2
(45) Date of Patent: Mar. 8, 2011

(54) ORGANOSILICONE COMPOSITIONS AND METHODS FOR PREPARING THEM

(75) Inventors: Joseph Edward Nesakumar, Bangalore (IN); Ganesh Kannan, Evansville, IN (US); Vikram Kumar, Tarrytown, NY (US); Hariharan Ramalingam, Bangalore (IN); Mark D. Leatherman, Stamford, CT (US); Suresh K. Rajaraman, Macungie, PA (US)

(73) Assignee: Momentive Performance Materials Inc., Albany, NY (US)

( * ) Notice: Subject to any disclaimer, the term of this patent is extended or adjusted under 35 U.S.C. 154(b) by 0 days.

(21) Appl. No.: 12/718,552

(22) Filed: Mar. 5, 2010

(65) Prior Publication Data

US 2010/0249358 A1  Sep. 30, 2010

Related U.S. Application Data

(62) Division of application No. 11/943,638, filed on Nov. 21, 2007, now abandoned.

(51) Int. Cl.
    C08G 77/04 (2006.01)
    C08G 77/06 (2006.01)
    C08G 77/12 (2006.01)
    C08G 77/18 (2006.01)
(52) U.S. Cl. ........ 528/27; 528/10; 528/25; 528/31; 528/33; 528/34
(58) Field of Classification Search .......... 528/27, 528/10, 25, 31, 33, 34
    See application file for complete search history.

(56) References Cited

U.S. PATENT DOCUMENTS

| | | | | |
|---|---|---|---|---|
| 3,825,618 A * | 7/1974 | Pepe | | 528/25 |
| 4,211,823 A * | 7/1980 | Suzuki et al. | | 428/412 |
| 5,426,151 A | 6/1995 | Brandt et al. | | |
| 6,248,854 B1 * | 6/2001 | Hohn et al. | | 528/25 |
| 6,313,255 B1 | 11/2001 | Rubinsztajn | | |
| 6,602,602 B1 * | 8/2003 | Crivello | | 428/402 |
| 6,828,404 B2 * | 12/2004 | Crivello | | 528/25 |
| 2003/0232900 A1 | 12/2003 | Irifune | | |
| 2006/0247408 A1 * | 11/2006 | Crivello | | 528/33 |

(Continued)

OTHER PUBLICATIONS

Dworak D P et al: "Synthesis of cycloaliphatic substituted silane monomers and polysiloxanes for photocuring" Dec. 14, 2004, Macromolecules 20041214 American Chemical Society US, vol. 37, NR. 25, pp. 9402-9417, XP002515362 figures 1,7; p. 9416, col. 1, paragraph 2.

(Continued)

Primary Examiner — Randy Gulakowski
Assistant Examiner — Robert Loewe
(74) Attorney, Agent, or Firm — Kenneth S. Wheelock

(57) ABSTRACT

Disclosed herein is a composition comprising a structure $(M^1)_a(M^E)_b(D^1)_c(D^2)_d(T)_e(Q)_f$, wherein $M^1=R^1R^2R^3SiO_{1/2}$; $M^E=R^4R^5R^ESiO_{1/2}$; $D^1=R^6R^7SiO_{2/2}$; $D^2=R^8R^9SiO_{2/2}$; $T=R^{10}SiO_{3/2}$; and $Q=SiO_{4/2}$; wherein each $R^E$ is independently a monovalent hydrocarbon radical containing an epoxy group; $R^9$ comprises a structure $-L^1-Si(R^{11})_g(OR^{12})_{3-g}$ or $L^2(D^3)_h(M^2)_i-L^3-Si(R^{13})_{g'}(OR^{14})_{3-g'}$, wherein $L^1$, $L^2$, and $L^3$ are independently divalent linking groups; g and g' independently have a value from 0 to 2; $M^2=R^{15}R^{16}R^{17}SiO_{1/2}$; $D^3=R^{18}R^{19}SiO_{2/2}$; wherein $R^1$, $R^2$, $R^3$, $R^4$, $R^5$, $R^6$, $R^7$, $R^8$, $R^{10}$, $R^{11}$, $R^{12}$, $R^{13}$, $R^{14}$, $R^{15}$, $R^{16}$, $R^{17}$, $R^{18}$, and $R^{19}$ are independently monovalent hydrocarbon radicals; wherein a, b, c, d, e, f, h, and i are stoichiometric subscripts that are zero or positive subject to the following limitations: b has a value of 2; d is greater than or equal to 1; when (a+c+e+f) is equal to zero, (b+d) is greater than or equal to 3; and when i=0, h is at least 1.

7 Claims, 4 Drawing Sheets

U.S. PATENT DOCUMENTS

2007/0287763 A1* 12/2007 Soucek et al. ............ 522/6
2008/0051525 A1* 2/2008 Soucek et al. ............ 525/477
2008/0064803 A1* 3/2008 Soucek et al. ............ 524/440
2008/0064832 A1* 3/2008 Deruelle et al. .......... 525/477
2008/0260337 A1* 10/2008 Bahadur et al. .......... 385/123

OTHER PUBLICATIONS

Dworak D P: "Protective space coatings: a ceramer approach for nanoscale materials" Progress in Organic Coatings, vol. 47, 2003, pp. 448-457, XP002515361 figures 1, 3, 5.

* cited by examiner

ORGANOSILICONE COMPOSITIONS AND METHODS FOR PREPARING THEM

CROSS REFERENCE TO RELATED APPLICATIONS

This application is a divisional of U.S. application Ser. No. 11/943,638, filed Nov. 21, 2007 which claims the benefit of U.S. Provisional Application Ser. No. 60/866,707, filed Nov. 21, 2006

BACKGROUND

The invention relates generally to compositions comprising an epoxy-capped organosilicone comprising at least one pendant functional organosilicon group. Further, the invention relates to methods for selectively preparing these compositions. Furthermore, the invention relates to polymer compositions comprising the products of reaction of these compositions with a polymer having at least one end-group reactive towards the epoxy-capped siloxane, such as carboxylic acid end-groups. Further still, the invention relates to various end-uses of the polymer compositions.

Organosilicones having epoxy groups as end-cappers and/or pendant groups are known in the art, and have been used in a variety of applications, such as for example, silicone-based epoxy resins. However, there still remains a need for organosilicones exclusively having epoxy end-capping groups and at least one pendant functional organosilicon group for forming more robust products for more demanding end-uses. Further still, there remains a need for methods to prepare such organosilicones in a selective manner.

BRIEF DESCRIPTION

One aspect of the invention is a composition comprising a structure $(M^1)_a(M^E)_b(D^1)_c(D^2)_d(T)_e(Q)_f$; wherein $M^1=R^1R^2R^3SiO_{1/2}$; $M^E=R^4R^5R^ESiO_{1/2}$; $D^1=R^6R^7SiO_{2/2}$; $D^2=R^8R^9SiO_{2/2}$; $T=R^{10}SiO_{3/2}$; and $Q=SiO_{4/2}$;
wherein each $R^E$ is independently a monovalent hydrocarbon radical containing an epoxy group; $R^9$ comprises a structure $-L^1-Si(R^{11})_g(OR^{12})_{3-g}$ or $L^2(D^3)_h(M^2)_iL^3-Si(R^{13})_{g'}(OR^{14})_{3-g'}$, wherein $L^1$, $L^2$, and $L^3$ are independently divalent linking groups; g and g' independently have a value from 0 to 2; $M^2=R^{15}-R^{16}R^{17}SiO_{1/2}$; $D^3=R^{18}R^{19}SiO_{2/2}$;
wherein $R^1$, $R^2$, $R^3$, $R^4$, $R^5$, $R^6$, $R^7$, $R^8$, $R^{10}$, $R^{11}$, $R^{12}$, $R^{13}$, $R^{14}$, $R^{15}$, $R^{16}$, $R^{17}$, $R^{18}$, and $R^{19}$ are independently monovalent hydrocarbon radicals;
wherein a, b, c, d, e, f, h, and i are stoichiometric subscripts that are zero or positive subject to the following limitations: b has a value of 2; d is greater than or equal to 1; when (a+c+e+f) is equal to zero, (b+d) is greater than or equal to 3; and when i=0, h is at least 1.

Another aspect of the invention is a composition comprising a structure: $(M^E)_j(D^4)_k(D^5)_l$, wherein $M^E=R^{20}R^{21}R^ESiO_{1/2}$; $D^4=R^{22}R^{23}SiO_{2/2}$; and $D^5=R^{24}R^{25}SiO_{2/2}$; wherein $R^{20}$, $R^{21}$, $R^{22}$, $R^{23}$, $R^{24}$, and $R^{25}$ are independently monovalent hydrocarbon radicals; each $R^E$ is independently a monovalent hydrocarbon radical containing an epoxy group, $R^{25}=-L^4-Si(R^{26})_m(OR^{27})_{3-m}$, wherein $L^4$ is a divalent linking group, m has a value from 0 to 2, and $R^{26}$ and $R^{27}$ are independently monovalent hydrocarbon radicals; j has a value of 2; k is zero or greater than 1, and l is greater than or equal to 1.

In still another aspect, a method for preparing a composition comprising a structure: $(M^1)_a(M^E)_b(D^1)_c(D^2)_d(T)_e(Q)_f$ is provided. The method comprises: (i) reacting an organosilicon hydride having a structure $(M^1)_a(M^H)_b(D^1)_c(T)_e(Q)_f$ with an epoxyolefin to form a first intermediate product having a structure $(M^1)_a(M^E)_b(D^1)_c(T)_e(Q)_f$; wherein $M^1=R^1R^2SiO_{1/2}$; $M^H=R^4R^5HSiO_{1/2}$; $D^1=R^6R^7SiO_{2/2}$; $T=R^{10}SiO_{3/2}$; $Q=SiO_{4/2}$; and $M^E=R^4R^5R^ESiO_{1/2}$; wherein $R^1$, $R^2$, $R^3$, $R^4$, $R^5$, $R^6R^7$, and $R^{10}$ are independently monovalent hydrocarbon radicals; each $R^E$ is independently a monovalent hydrocarbon radical containing an epoxy group; and a, b, c, e, and f are stoichiometric subscripts that are zero or positive subject to the limitation that b has a value of 2; and when (a+c+e+f)=0, b=2;

(ii) reacting the first intermediate product with a cyclic siloxane having a structure $(D^6)_n$ to form a second intermediate product having a structure $(M^1)_a(M^E)_b(D^1)_c(D^6)_o(T)_e(Q)_f$; wherein $D^6$ is $R^8R^{28}SiO_{2/2}$, wherein $R^8$ is a monovalent hydrocarbon radical, $R^{28}$ is a monovalent alkenyl group; a, b, c, e, f, n, and o are stoichiometric subscripts that are zero or positive, subject to the following limitations: n is greater than or equal to 3; o is at least 1; b has a value of 2; and when (a+c+e+f) is equal to zero, (b+o) is greater than or equal to 3; and (iii) reacting the second intermediate product with an (alkoxy)hydrosilane to form the composition having a structure $(M^1)_a(M^E)_b(D^1)_c(D^2)_d(T)_e(Q)_f$; wherein $M^1=R^1R^2R^3SiO_{1/2}$; $M^E=R^4R^5R^ESiO_{1/2}$; $D^1=R^6R^7SiO_{2/2}$; $D^2=R^8R^9SiO_{2/2}$; $T=R^{10}SiO_{3/2}$; and $Q=SiO_{4/2}$; wherein each $R^E$ is independently a monovalent hydrocarbon radical containing an epoxy group; $R^9$ comprises a pendant functional organosilicon group comprising a structure $-L^1-Si(R^{11})_g(OR^{12})_{3-g}$ or $L^2(D^3)_h(M^2)_iL^3-Si(R^{13})_{g'}(OR^{14})_{3-g'}$, wherein $L^1$, $L^2$, and $L^3$ are independently divalent linking groups; g and g' independently have a value from 0 to 2; $M^2=R^{15}R^{16}R^{17}SiO_{1/2}$; $D^3=R^{18}R^{19}SiO_{2/2}$;
wherein $R^1$, $R^2$, $R^3$, $R^4$, $R^5$, $R^6$, $R^7$, $R^8$, $R^{10}$, $R^{11}$, $R^{12}$, $R^{13}$, $R^{14}$, $R^{15}$, $R^{16}$, $R^{17}$, $R^{18}$, and $R^{19}$ are independently monovalent hydrocarbon radicals;
wherein a, b, c, d, e, f, h, and i are stoichiometric subscripts that are zero or positive subject to the following limitations: b has a value of 2; d is greater than or equal to 1; when (a+c+e+f) is equal to zero, (b+d) is greater than or equal to 3; and when i=0, h is at least 1.

In other aspects, polymer compositions and coating compositions comprising the products of reaction of the compositions disclosed hereinabove and a polymer having at least one carboxylic acid end-group are provided.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
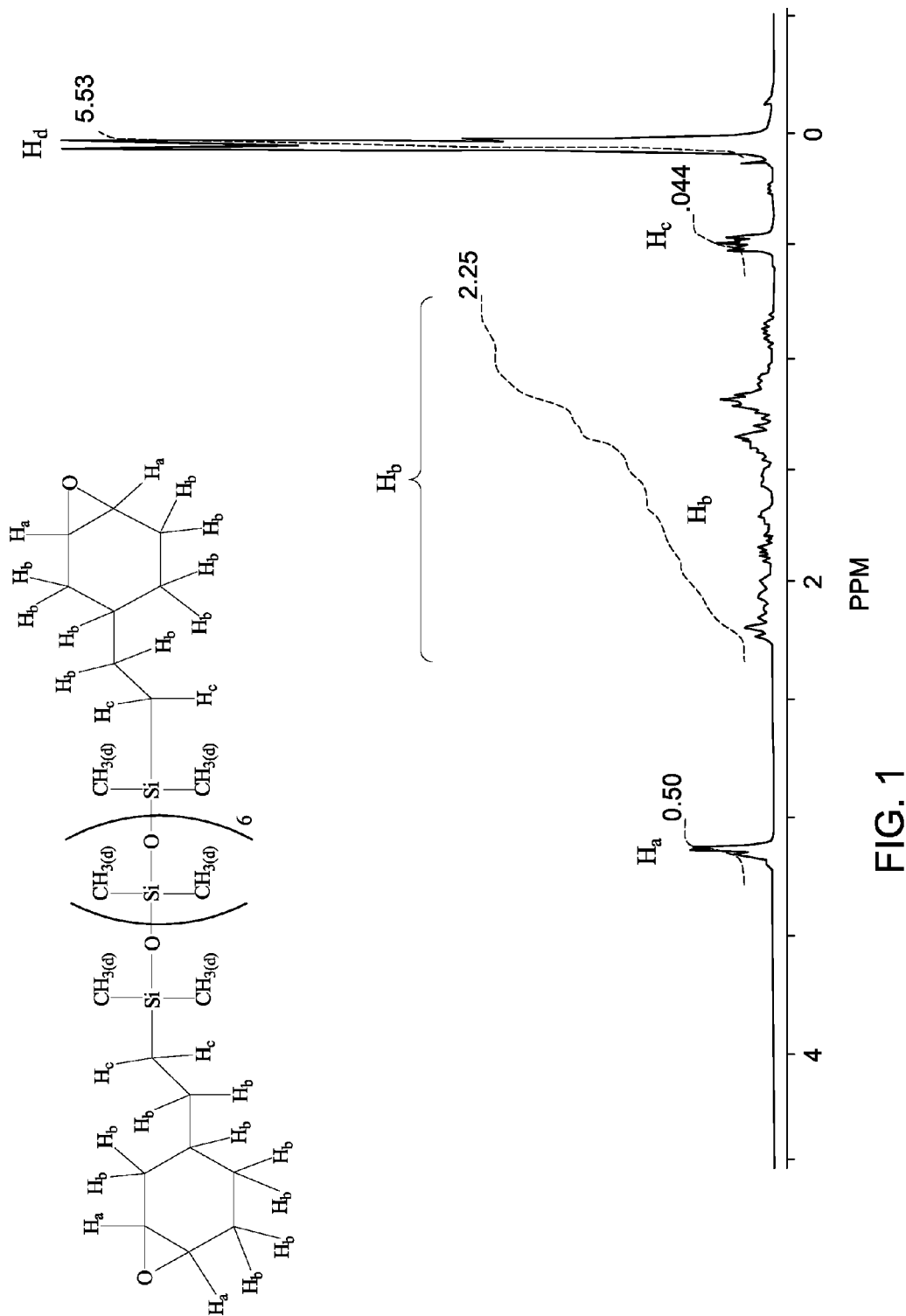
FIG. 1 represents a proton nuclear magnetic resonance spectrum with peak assignments for the first intermediate product $M^E(D)_6M^E$, described in Example 1.

These and other features, aspects, and advantages of the present invention will become better understood in light of the following detailed description The singular forms "a", "an" and "the" include plural referents unless the context clearly dictates otherwise.

"Optional" or "optionally" means that the subsequently described event or circumstance may or may not occur, and that the description includes instances where the event occurs and instances where it does not.

As defined herein, the terms "radical" and "group", as applied to the terms "alkyl", "cycloalkyl", "aryl", "alkoxy", "aryloxy", and "cycloalkoxy" are used interchangeably throughout this disclosure.

As defined herein, the term "monovalent hydrocarbon radical" represents any of a monovalent alkyl radical, a monovalent cycloalkyl radical, or a monovalent aryl radical. Unless otherwise specified, the term "hydrocarbon radical" is meant to include those radicals having one to sixty carbon atoms. Further, the hydrocarbon radicals may comprise heteroatoms, such as sulfur, oxygen, and nitrogen.

As defined herein, the term "alkyl" refers to a monovalent array of carbon atoms that is not cyclic and is attached to the silicon atom via an $sp^3$ carbon atom. The array of carbon atoms may further comprise any combination of $sp^3$, $sp^2$, or sp hybridized carbon atoms. The array of carbon atoms may further comprise one or more heteroatoms, such as oxygen, nitrogen, and sulfur. Furthermore, the alkyl radical or group can comprise other functional groups, such as for example, hydroxy groups. Examples of alkyl groups include methyl, ethyl, n-propyl, isopropyl, n-butyl, tert-butyl, isooctyl, benzyl, cyclohexylmethyl, phenethyl, 3-hydroxypropyl, butoxy, 2-hydroxyethyl, alpha,alpha-dimethylbenzyl, and the like.

As defined herein, the term "alkoxy" means any monovalent alkyl radical, as described above, attached to an oxygen atom.

As defined herein, the term "aryl" refers to a monovalent cyclic array of $sp^2$ hybridized carbon atoms and conjugated carbon-carbon double bonds, and is attached to the silicon atom via an $sp^2$ hybridized carbon atom. The aromatic group or radical can have from one to the maximum permissible number of substituents. The aryl or aromatic radical or group can further comprise heteroatoms, such as sulfur, oxygen, and nitrogen. Furthermore, the aromatic radical or group can comprise other functional groups, such as for example, hydroxy groups. Examples of aryl groups include phenyl, substituted phenyl, tolyl, substituted tolyl, xylyl, mesityl, chlorophenyl, naphthyl, furyl, furylmethyl, thienyl, pyrrolyl, 2-hydroxyphenyl, 4-hydroxyphenyl, and the like.

As defined herein, the term "cycloalkyl" refers to a monovalent cyclic array of carbon atoms, and is attached to the silicon atom via an sp3 hybridized carbon atom that forms part of the cyclic array of carbon atoms. The cyclic array of carbon atoms may further comprise one or more heteroatoms, such as oxygen, sulfur, and nitrogen. Further, the cyclic array of carbon atoms can be substituted with one to the maximum permissible number of substituents. Furthermore, the cycloalkyloxy group or radical can comprise other functional groups, such as for example, hydroxy groups. Examples of cycloalkyl groups include cyclohexyl, methylcyclohexyl, trimethylcyclohexyl, phenylcyclohexyl, tetrahydropyranyl, 4-hydroxycyclohexyl, 4-thiacyclohexyl, cyclooctyl, and the like.

As defined herein, the term "monovalent alkenyl" group or radical refers to an olefinic group that is attached to the silicon atom. The alkenyl groups can comprise an alkyl group, an aryl group, or a cycloalkyl group. Further, the alkenyl group can be attached to the silicon atom through an $sp^2$ or an $sp^3$ hybridized carbon atom. Some examples of alkenyl groups include vinyl or ethenyl, 1-propenyl, 1-butenyl, 1-hexenyl, styrenyl, and methallyl.

As defined herein, the term "epoxy-capped" as applied to an organosilicone refers to an organosilicone polymer having one epoxy-containing organic group at each end of an organosilicone polymer.

In an embodiment of the invention, compositions having a structure (I),

wherein $M^1=R^1R^2R^3SiO_{1/2}$; $M^E=R^4R^5R^ESiO_{1/2}$; $D^1=R^6R^7SiO_{2/2}$; $D^2=R^8R^9SiO_{2/2}$; $T=R^{10}SiO_{3/2}$; and $Q=SiO_{4/2}$;

wherein each $R^E$ is independently a monovalent hydrocarbon radical containing an epoxy group; $R^9$ comprises a pendant functional organosilicon group comprising a structure $-L^1-Si(R^{11})_g(OR^{12})_{3-g}$ or $L^2(D^3)_h(M^2)_i-L^3-Si(R^{13})_{g'}(OR^{14})_{3-g'}$, wherein $L^1$, $L^2$, and $L^3$ are independently divalent linking groups; g and g' independently have a value from 0 to 2; $M^2=R^{15}R^{16}R^{17}SiO_{1/2}$; $D^3=R^{18}R^{19}SiO_{2/2}$;

wherein $R^1$, $R^2$, $R^3$, $R^4$, $R^5$, $R^6$, $R^7$, $R^8$, $R^{10}$, $R^{11}$, $R^{12}$, $R^{13}$, $R^{14}$, $R^{15}$, $R^{16}$, $R^{17}$, $R^{18}$, and $R^{19}$ are independently monovalent hydrocarbon radicals;

wherein a, b, c, d, e, f, h, and i are stoichiometric subscripts that are zero or positive subject to the following limitations: b has a value of 2; d is greater than or equal to 1; when (a+c+e+f) is equal to zero, (b+d) is greater than or equal to 3; and when i=0, h is at least 1.

In an embodiment, $R^1$, $R^2$, $R^3$, $R^4$, $R^5$, $R^6$, $R^7$, $R^8$, $R^{10}$, $R^{11}$, $R^{12}$, $R^{13}$, $R^{14}$, $R^{15}$, $R^{16}$, $R^{17}$, $R^{18}$, and $R^{19}$ are independently monovalent hydrocarbon radicals. Non-limiting examples of alkyl radicals include methyl, ethyl, sec-butyl, tert-butyl, octyl, decyl, dodecyl, cetyl, butoxy, hydroxypropyl, 2,5,8-trioxadecyl, triacontyl, and 3,3,3-trifluoropropyl. In another embodiment, $R^1$, $R^2$, $R^3$, $R^4$, $R^5$, $R^6$, $R^7$, $R^8$, $R^{10}$, $R^{11}$, $R^{12}$, $R^{13}$, $R^{14}$, $R^{15}$, $R^{16}$, $R^{17}$, $R^{18}$, and $R^{19}$ are independently selected from the group consisting of alkyl radicals and aryl radicals. Some non-limiting examples include compositions where $R^6$ and $R^7$ are aryl radicals, such as phenyl radicals; and $R^1$, $R^2$, $R^3$, $R^4$, $R^5$, $R^8$, $R^{10}$, $R^{11}$, $R^{12}$, $R^{13}$, $R^{14}$, $R^{15}$, $R^{16}$, $R^{17}$, $R^{18}$, and $R^{19}$ are independently alkyl radicals, such as for example, methyl, ethyl, and propyl.

Structure (I) comprises at least one pendant functional organosilicon group, denoted as $R^9$ in structure (I). The functional organosilicon group generally comprises reactive groups that are capable of forming covalent bonds with other reactive functional groups. The reactive groups comprise an alkoxy group, an aryloxy group, a cycloalkoxy group, a thioalkoxy group, a thioaryloxy group, or a thiocycloalkoxy group. In an embodiment, the functional organosilicon group $R^9$ is an (alkoxysilyl)alkyl group having a general structure (II),

wherein $L^1$ is a divalent linking group; g has a value from 0 to 2, and $R^{11}$ and $R^{12}$ are independently monovalent hydrocarbon radicals. In an embodiment, the divalent linking group $L^1$ is derived from a monovalent alkenyl group. Non-limiting examples of $L^1$ include those selected from the group consisting of 1-ethenyl (also sometimes called as vinyl), 1-propenyl, 1-butenyl, 1-pentenyl, and styrenyl. In a particular embodiment, the monovalent alkenyl group is a vinyl group. $R^{11}$ and $R^{12}$ are independently monovalent alkyl radicals, monovalent aryl radicals, or monovalent cycloalkyl radicals. In an embodiment, $R^{11}$ and $R^{12}$ are independently selected from the group consisting of methyl, ethyl, propyl, n-butyl, cyclohexyl, phenyl, benzyl, sec-butyl, tert-butyl, octyl, decyl, butoxy, dodecyl, cetyl, hydroxypropyl, 2,5,8-trioxadecyl, triacontyl, and 3,3,3-trifluoropropyl.

In another embodiment, the pendant functional organosilicon group $R^9$ comprises a structure (III),

(III)

wherein $L^2$, and $L^3$ are independently divalent linking groups; g and g' independently have a value from 0 to 2; and $D^3 = R^{18}R^{19}SiO_{2/2}$; wherein $R^{13}$, $R^{14}$, $R^{15}$, $R^{16}$, $R^{17}$, $R^{18}$, and $R^{19}$ are independently monovalent hydrocarbon radicals having one to sixty carbon atoms; and h and i are stoichiometric subscripts that are zero or positive subject to the following limitations: when i=0, h is at least 1. The linking groups $L^2$ and $L^3$ can be the same or different divalent alkyl groups. The divalent alkyl groups can be derived from monovalent alkenyl groups. Non-limiting examples of $L^1$, $L^2$, and $L^3$ include those independently selected from the group consisting of 1-ethenyl (also sometimes called as vinyl), 1-propenyl, 1-butenyl, 1-pentenyl, and styrenyl. More particularly, the linking groups $L^1$, $L^2$, and $L^3$ are each a vinyl radical. The monovalent hydrocarbon radicals $R^{13}$, $R^{14}$, $R^{15}$, $R^{16}$, $R^{17}$, $R^{18}$, and $R^{19}$ are independently selected from alkyl radicals, cycloalkyl radicals, and aryl radicals. In an embodiment, $R^{13}$, $R^{14}$, $R^{15}$, $R^{16}$, $R^{17}$, $R^{18}$, and $R^{19}$ are independently selected from the group consisting of methyl, ethyl, propyl, n-butyl, cyclohexyl, phenyl, benzyl, sec-butyl, tert-butyl, 3-hydroxypropyl, butoxy, octyl, decyl, dodecyl, and cetyl. An example of the pendant functional organosilicon group $R^9$ falling within the scope of the general structure (III) has a structure (IV)

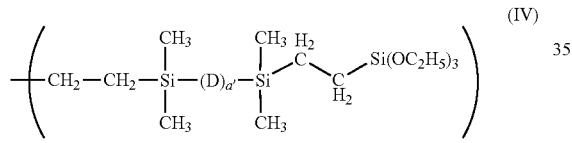

(IV)

wherein a' has a value from 1 to 500, and $D=(CH_3)_2SiO$.

The compositions comprise up to two monovalent hydrocarbon radicals each containing an epoxy group. These radicals, represented as $R^E$ in structure (I) have a general structure (V),

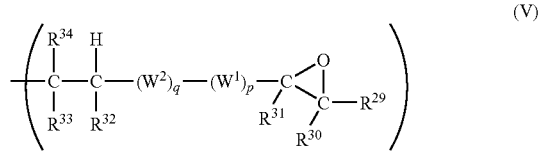

(V)

wherein $R^{29}$, $R^{30}$, $R^{31}$, $R^{32}$, $R^{33}$, and $R^{34}$ are independently selected from the group consisting of hydrogen atom and monovalent hydrocarbon radicals having from one to sixty carbon atoms, $W^1$ is a divalent or a trivalent hydrocarbon radical having from one to sixty carbon atoms, $W^2$ is a divalent hydrocarbon radical having from one to sixty carbon atoms, and subscripts p and q are independently zero or one subject to the limitation that when $W^1$ is trivalent, one of $R^{29}$ or $R^{31}$ is a hydrogen atom. In an embodiment, $R^E$ is selected from the group consisting of structures (VI), (VII), (VIII), (IX), (X), and (XI)

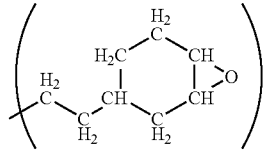

(VI)

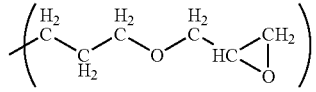

(VII)

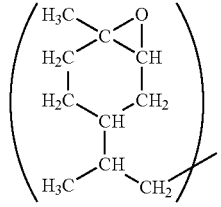

(VIII)

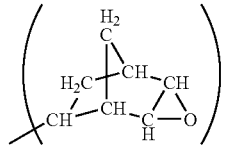

(IX)

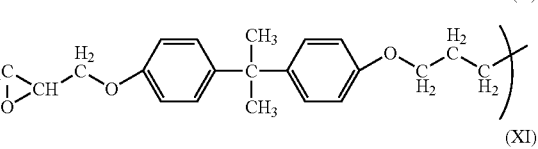

(X)

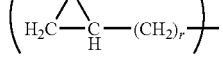

(XI)

wherein r has a value from 2 to 20. In a particular embodiment, $R^E$ is structure (VI) since it can be readily derived from the commercially available 4-vinylcyclohexene.

In another embodiment, $R^E$ has a structure (V), wherein $R^{29}$, $R^{30}$, $R^{31}$, $R^{32}$, $R^{33}$, and $R^{34}$ are hydrogen; and p and q are zero.

The compositions represented by structure (I) generally encompass compounds wherein b has a value of 2. In an embodiment, when b is 2, d is greater than or equal to 1. Some non-limiting examples of compositions that fall within the scope of structure (I) have the structure (XII).

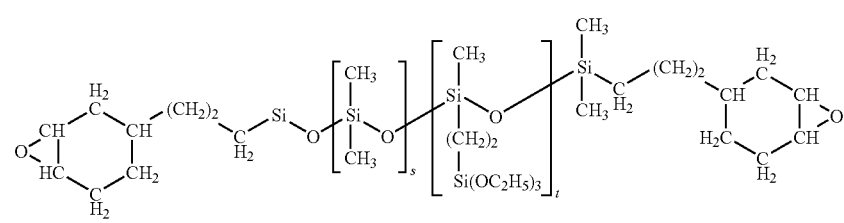

(XII)

In other embodiments, compositions have structure (XII) wherein s is about 6 and t is about 3; s is zero and t is about 3 in another embodiment; and s is about 6 and t is about 7.

In another embodiment, compositions disclosed herein comprise a structure (XIII),

wherein $M^E = R^{20}R^{21}R^E SiO_{1/2}$; $D^4 = R^{22}R^{23}SiO_{2/2}$; and $D^5 = R^{24}R^{25}SiO_{2/2}$; wherein $R^{20}$, $R^{21}$, $R^{22}$, $R^{23}$, $R^{24}$, and $R^{25}$ are independently monovalent hydrocarbon radicals; each $R^E$ is independently a monovalent hydrocarbon radical containing an epoxy group, $R^{25} = -L^4-Si(R^{26})_m(OR^{27})_{3-m}$, wherein $L^4$ is a divalent linking group, m has a value from 0 to 2, and $R^{26}$ and $R^{27}$ are independently monovalent hydrocarbon radicals; j has a value of 2; k is zero or greater than 1, and 1 is greater than or equal to 1. Further, the composition shown in structure (XIII) may independently comprise T and Q units, which are defined in a similar manner as done previously for structure (I). In an embodiment, the compositions of structure (XIII) comprise $R^E$ having structure (VI) due to the ready availability of 4-vinylcyclohexene epoxide.

The compositions having structure (I) can be readily prepared by a method as follows. First, an organosilicon hydride having a structure (XIV)

is reacted with an epoxyolefin to form a first intermediate product having a structure (XV),

wherein $M^1 = R^1R^2R^3SiO_{1/2}$; $M^H = R^4R^5HSiO_{1/2}$; $D^1 = R^6R^7SiO_{2/2}$; $T = R^{10}SiO_{3/2}$; $Q = SiO_{4/2}$; and $M^E = R^4R^5R^E SiO_{1/2}$; wherein $R^1$, $R^2$, $R^3$, $R^4$, $R^5$, $R^6$, $R^7$, and $R^{10}$ are independently monovalent hydrocarbon radicals; each $R^E$ is independently a monovalent hydrocarbon radical containing an epoxy group; and a, b, c, e, and f are stoichiometric subscripts that are zero or positive subject to the following limitations: b has a value of 2; and when (a+c+e+f) is equal to zero, b is equal to 2.

Any organosilicon hydride having one or two terminal Si—H bonds can be used for the hydrosilylation of the epoxyolefins. For preparing first intermediate products wherein b in structure (XV) is 2, a variety of hydride-capped organosilicones (that is, each end of the linear organosilicone has one Si—H bond) can be used as the organosilicon hydride. Any of the commercially available hydride-capped organosilicones can be used.

Suitable epoxyolefins are represented by a general structure (XVI),

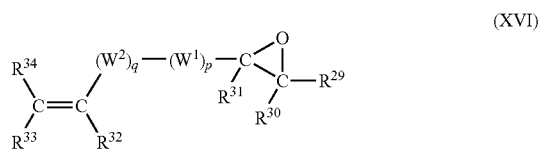

wherein $R^{29}$, $R^{30}$, $R^{31}$, $R^{32}$, $R^{33}$, and $R^{34}$ are independently selected from the group consisting of hydrogen atom and monovalent hydrocarbon radicals having from one to sixty carbon atoms, $W^1$ is a divalent or a trivalent hydrocarbon radical having from one to sixty carbon atoms, $W^2$ is a divalent hydrocarbon radical having from one to sixty carbon atoms, and subscripts p and q are independently zero or one subject to the limitation that when $W^1$ is trivalent, one of $R^{29}$ or $R^{30}$ is a hydrogen atom.

Specific examples of epoxyolefins are shown in structures (XVII) to (XXII).

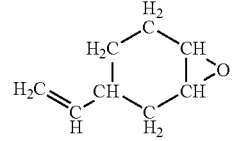

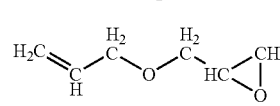

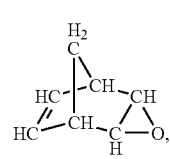

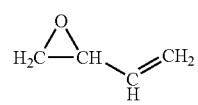

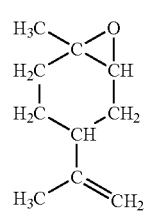

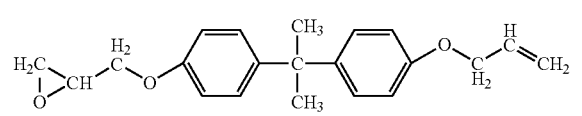

In an embodiment, the epoxyolefin is selected from the group consisting of limonene oxide, 1,2-epoxy-7-octene, 1,2-epoxy-9-decene, 1,2-epoxy-4-vinylcyclohexane, 1,2-epoxy-5-hexene, 1,2-epoxy-9-decene, 3,4-epoxy-1-butene, allyl glycidyl ether, 1,2-epoxy-7-octene, 2,3-epoxy-5,6-norbornene, and 2-(4-allyloxyphenyl)-2-(4-glycidyloxyphenyl) propane, or mixtures thereof.

Next, the first intermediate product obtained as described above is reacted with a cyclic siloxane having a structure (XXIII)

 

to form a second intermediate product having a structure $(M^1)_a(M^E)_b(D^1)_c(D^6)_o(T)_e(Q)_f$; wherein $D^6$ is $R^8R^{28}SiO_{2/2}$, wherein $R^8$ is a monovalent hydrocarbon radical, $R^{28}$ is a monovalent alkenyl group; and a, b, c, e, and f, are stoichiometric subscripts that are zero or positive, and n and o are stoichiometric subscripts that are positive subject to the following limitations: n is greater than or equal to 3, b has a value of 2; d is greater than or equal to 1; and when (a+c+e+f) is equal to zero, (b+o) is greater than or equal to 3. The cyclic siloxane comprises a cyclic (organoalkenyl)siloxane. Any cyclic (organoalkenyl)siloxane wherein each silicon atom has one alkyl group and one alkenyl group can be used. Non-limiting examples of cyclic siloxanes of structure (XXII) include tetramethyltetravinylcyclotetrasiloxane; tetrapropyltetravinylcyclotetrasiloxane, tetraallyltetraethylcyclotetrasiloxane, and tetraoctyltetravinylcyclotetrasiloxane. A catalyst is generally used to facilitate this reaction. Alkali metal hydroxides, such as for example, cesium hydroxide can be used to form the second intermediate product.

The second intermediate product is next reacted with an (alkoxy)hydrosilane whereby the alkenyl groups are hydrosilylated by the Si—H bond of the (alkoxy)hydrosilane to form the desired compositions having general structure (I). Generally, any compound having one Si—H bond and at least one silicon-alkoxy bond situated anywhere in the compound can be regarded as the (alkoxy)hydrosilane useful for the third step. In an embodiment, the (alkoxy)hydrosilane has a structure (XXIII),

wherein $R^{11}$ and $R^{12}$ are independently monovalent hydrocarbon radicals; and g has a value from zero to 2. The (alkoxy)hydrosilane (XXIII) reacts with the second intermediate product to form the desired composition comprising a structure $(M^1)_a(M^E)_b(D^1)_c(D^2)_d(T)_e(Q)_f$ wherein $M^1=R^1R^2R^3SiO_{1/2}$; $M^E=R^4R^5R^ESiO_{1/2}$; $D^1=R^6R^7SiO_{2/2}$; $D^2=R^8R^9SiO_{2/2}$; $T=R^{10}SiO_{3/2}$; and $Q=SiO_{4/2}$; wherein $R^1$, $R^2$, $R^3$, $R^4$, $R^5$, $R^6$, $R^7$, $R^8$, and $R^{10}$ are independently monovalent hydrocarbon radicals; each $R^E$ is independently a monovalent hydrocarbon radical containing an epoxy group; and $R^9$ comprises $-L^1-Si(R^{11})_g(OR^{12})_{3-g}$, wherein $L^1$ is derived from the alkenyl group $R^{28}$ in the second intermediate product having structure $(M^1)_a(M^E)_b(D^1)_c(D^6)_o(T)_e(Q)_f$ (described previously), and $R^{11}$, $R^{12}$, and g are as described for structure (XXIII).

The (alkoxy)hydrosilane can also have a structure (XXIV),

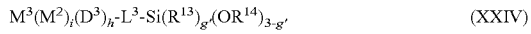

wherein $L^3$, g, and g' are as explained previously for structure (III); $M^2=R^{15}R^{16}R^{17}SiO_{1/2}$; $D^3=R^{18}R^{19}SiO_{2/2}$; and $M^3=HR^{35}R^{36}SiO_{2/2}$; wherein $R^{15}$, $R^{16}$, $R^{17}$, $R^{18}$, $R^{19}$, $R^{35}$, and $R^{36}$ are independently monovalent hydrocarbon radicals; and wherein h and i are stoichiometric subscripts that are zero or positive subject to the following limitations: when i=0, h is at least 1.

The (alkoxy)silane compounds having structure (XXIV) can be prepared, for example from an (alkenyl)alkoxysilane by selectively hydrosilylating one end of a hydride-capped siloxane (that is, a siloxane having one Si—H bond at each end of the siloxane). A rhodium catalyst may be used to achieve this type of selectivity. The (alkoxy)hydrosilane having the structure (XXIV) can then be reacted with the second intermediate product (described previously) to produce the desired composition having structure (I). An example of a (alkoxy)hydrosilane having the structure (XXIV) is shown in structure (XXV) which can be prepared by a synthetic approach shown in Equation (1),

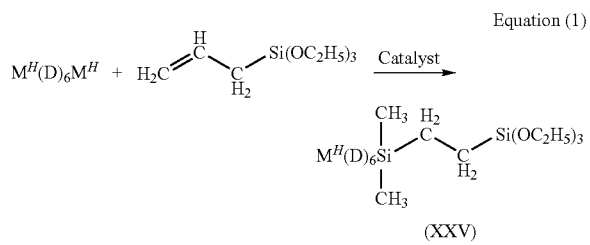

where $M^H=H(CH_3)_2SiO_{1/2}$; and $D=(CH_3)_2SiO_{2/2}$. In this example, the linking group $L^3$ is derived from the allyl group of the reactant allyltriethoxysilane. When the (alkoxy)silane (XXV) reacts with the second intermediate product having structure $(M^1)_a(M^E)_b(D^1)_c(D^6)_o(T)_e(Q)_f$ (described previously), the linking group $L^2$ is derived from the alkenyl group $R^{28}$ of the $D^6$ unit of the second intermediate product reacting with the $M^H$ unit of structure (XXV).

The third step involving hydrosilylation of the alkenyl group $R^{28}$ in the second intermediate product by the (alkoxy)hydrosilane is usually carried out in the presence of a catalyst. The catalyst can be a free radical catalyst, such as an organic peroxide or an organic azo compound. Examples of peroxide catalysts include benzoyl peroxide, 2,5-dimethyl-2,5-di(tert-butylperoxy)hexane, and the like. The catalyst can also be an organometallic complex of a transition metal, such as platinum, which is generally used as a hydrosilylation catalyst. Rhodium catalysts may also be used. Usually, the platinum catalyst is introduced in a latent form such that the active form can be generated by application of an external stimulus, such as thermal energy or photochemical energy. For example, a platinum complex of 1-ethynyl-cyclohexan-1-ol can be used as the latent form of the catalyst. When the hydrosilylation reaction mixture is heated, the platinum complex releases 1-ethynyl-cyclohexan-1-ol, thereby releasing an active form of the platinum catalyst. Other catalysts known in the art, such as for example, sodium propionate can also be used. Mixtures of catalysts can also be used. Any alkoxysilane having at least one alkoxy group and a Si—H bond can be used. Non-limiting examples of (alkoxy)hydrosilanes having a Si—H bond includes trimethoxysilane, triethoxysilane, triphenoxysilane, and tributoxysilane.

The method described hereinabove can be used for preparing compositions having structure (I), wherein e and f are zero, a is 1 or 2 with the limitation that (a+b)=2; and c has a value from 0-500. In another embodiment, the method can be used for preparing compositions having structure (I) by selecting a cyclic siloxane having the structure (XXIII) wherein $R^8$ is selected from the group consisting of methyl, ethyl, sec-butyl, tert-butyl, octyl, decyl, dodecyl, cetyl, hydroxypropyl, butoxy, 2,5,8-trioxadecyl, triacontyl, and 3,3,3-trifluoropropyl; $R^{28}$ is selected from the group consisting of 1-ethenyl, 1-propenyl, 1-butenyl, 1-pentenyl, and styrenyl; and n has a value of 3-6. More particularly, the method can be used with a cyclic siloxane having structure (XXIII) wherein $R^8$ is methyl, $R^{28}$ is 1-ethenyl, and n is 4.

The compositions represented by structures such as (I) and (XIII) are valuable for producing a variety of polymer compositions. The polymer compositions comprise reaction products resulting from reaction of the epoxy terminal group(s) and the pendant (alkoxysilyl)alkyl groups of structures (I) or (XIII) with a polymer having at least one functional group reactive towards the epoxy and/or the (alkoxysilyl)alkyl groups. A variety of functional groups can react with an epoxy group. Non-limiting examples of functional groups that can react with an epoxy group include carboxyl-containing groups, amine groups, mercaptan groups, and hydroxy groups. Reactive amine groups include primary and secondary amine groups; and reactive hydroxy groups include aromatic hydroxy groups (or phenolic OH groups), aliphatic hydroxy groups, or cycloaliphatic hydroxy groups. Some examples of reactive carboxyl-containing functional groups include carboxylic acid groups, carboxyl ester groups, and carboxamide groups. Carboxylic acid functional groups are particularly useful since they can form ester linkages upon reaction with the epoxy groups. Thus in an embodiment, the silicone compositions having the structure (I) or (XIII) can function as chain extenders for polyesters having reactive end groups, such as carboxylic acid groups. The polymer reactive towards the epoxy groups can comprise aliphatic, aromatic, or cycloaliphatic carboxylic acid functional groups. Further, the polymer that is reactive towards the epoxy group can comprise one carboxylic acid functional group in an embodiment, and two carboxylic acid functional groups in another embodiment. With one carboxylic acid functional group, chain extension occurs at one end of the silicone compositions (I) or (XIII), whereas with two carboxylic acid groups, chain extension occurs at both ends of the silicone compositions. Examples of polymers having carboxylic acid endgroups include various polyesters. Such polyesters can be easily prepared by adjusting the relative stoichiometry of the dicarboxylic acid and dihydroxy compound using techniques known in the art. Some specific examples of useful polyesters that can be used to prepare chain-extended polymer compositions from the compositions having the structure (I) or (XIII) have the structures (XXVI) and (XXVII).

used for various end uses, such as for example, weatherable coatings, corrosion-resistant coatings, and chemically resistant coatings. Further, the compositions having structures (I) or (XIII) can be structured with aliphatic epoxy resins, silicone intermediates, alkoxysilanes and aminosilanes to provide other useful types of polymer compositions. The amine group of the aminosilane cures the epoxy resin in the usual manner and also participates in hydrolytic polycondensation reactions with silicone and alkoxysilane components. Further, coatings that maintain long term flexibility can be produced, which makes them attractive for forming durable protective coatings. The coating can be applied by brush, roll and airless or conventional spray. The coating compositions disclosed herein potentially have excellent adhesion to steel and compatibility with inorganic substrates. Without being bound

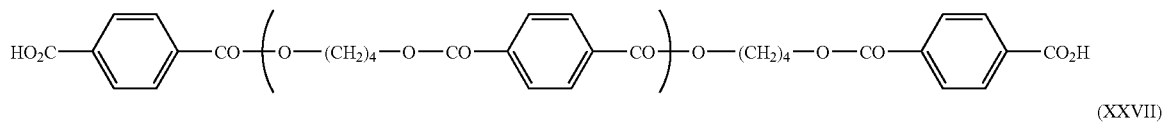

(XXVI)

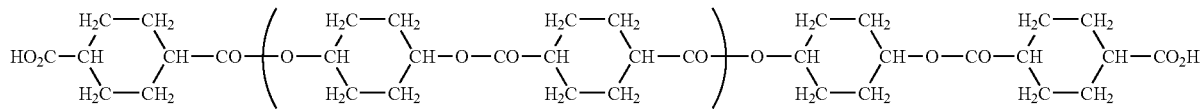

(XXVII)

The chain extended polymers, such as chain extended polyesters generally have improved toughness and improved chemical resistance as compared to the base polyester. Other useful polymers that may be used include those prepared by polymerizing monomers having a hydroxy group and a carboxylic acid group.

Amine terminated polymers can also function as polymers that can chain-extend the compositions having structures (I) and (XIII). For example, primary or secondary amine end groups in a polymer can react with the epoxy group to form useful reaction products. Such reaction products can have good properties, such as adhesion to metal surfaces, thereby making them valuable for coating applications, such as for example protecting metal surfaces.

A combination of (i) the reaction of the epoxy groups in structures (I) or (XIII) with various reactive functional groups, as described previously, and (ii) further reaction of the pendant (alkoxysilyl)alkyl groups provides a variety of cross-linked products valuable for various end-use applications. Further transformation of the (alkoxysilyl)alkyl groups can be carried out under conditions known in general for reacting an alkoxy group bonded to silicon. Since the (alkoxysilyl)alkyl group can have up to 3 alkoxy groups, as described in general structure (II) or (III), various degrees of cross-linking can be achieved. The alkoxy groups of the (alkoxysilyl)alkyl groups can either self-condense to form a cross-linked silicone polymer network. Alternatively, the alkoxy groups of the (alkoxysilyl)alkyl groups can be reacted with other silicone resins containing alkoxy groups to provide novel types of cross-linked silicone products. Therefore, in an embodiment, useful polymer compositions comprise reaction products resulting from reactions (i) and (ii). For example, useful polymer compositions have a structure comprising a chain-extended polyester and a cross-linked silicone network.

The polymer compositions described hereinabove are generally valuable for producing coatings. The coatings can be by any theory, it is believed that the high adhesion can be attributed to excellent wetting characteristics as well as an ability to function as an adhesion promoter. The alkoxysilane groups of the pendant (alkoxysilyl)alkyl groups hydrolyze and react with hydroxyl groups on metal inorganic substrates to form chemical bonds in a manner similar to the well-known silane adhesion promoters. The coating material can also be applied to sand-blasted steel surfaces and rusted steel without necessarily cleaning and preparing the surface. Organic primers may be used prior to application of the coating compositions comprising the coating compositions disclosed herein. Inorganic primers, such as zinc silicate may also be used.

In other applications, the epoxy-capped compositions can be used as a gloss-modifying additive. For example, when the epoxy-capped composition is blended with an impact modifier, such as ABS, and a polymer, such as polybutylene terephthalate in an extruder, the resulting material has reduced gloss as compared with the blend prepared without the epoxy-capped compositions. Such polymeric materials having reduced gloss are useful for automotive interiors, such as front panels.

The coating compositions can also potentially provide good resistance to alkali and solvents. Further, these coatings potentially have excellent weatherability, which can make them suitable for exterior coating applications. Such coatings are expected to show little or no chalking, cracking, embrittlement or color fade, and maintain or modify gloss over an extended period of time. In an embodiment, such durable coatings can be achieved by using compositions comprising structures (I) or (XIII) comprising long linear silicone chains. Thus in an embodiment, such coating compositions can exhibit good color hold and gloss retention, while also retaining good corrosion or chemical resistance. In an embodiment, the cross-linking density of the coating composition can be controlled by using the appropriate (alkoxyalkyl)silane functional group in the structures (I) or (XIII). Such an approach can lead to coatings that can have improved adhesion, and/or improved chemical resistance and/or improved humidity resistance. By an appropriate choice of the hydrocarbon radicals on the siloxane chain portion of structures (I) or (XIII), it is possible to produce coatings having flexibility and/or modified gloss retention.

Many other end-use applications of the coating compositions described herein are possible. In addition to coating metals, they can be used for coating materials such as plastics, fabrics, and paper. For paper applications, they can be used as paper release agents and as a paper-sizing aide. They can also be generally used for producing stain-resistant coatings.

EXAMPLES

Example 1

Procedure for Preparing the Epoxy-Capped Organosilicone $M^E(D)_6(D^7)_3M^E$

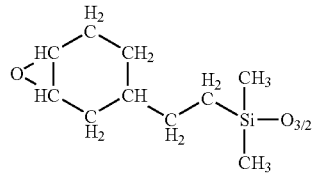

wherein $M^E=$, $D=(CH_3)_2SiO_{2/2}$; and $D^7=(C_2H_5O)_3SiCH_2CH_2Si(CH_3)-O_{2/2}$. The hydrosilylating agent used in this procedure has a structure $M^H(D)_6M^H$, wherein $M^H=H(CH_3)_2Si-O_{3/2}$; and D is as defined above for $M^E(D)_6(D^7)_3M^E$.

To hydride-capped polydimethylsiloxane $M^H(D)_6M^H$ (20 grams) taken in a 100 milliliter two-necked round-bottomed flask, triethylamine (20 microliters), dichloromethane (6 milliliters), and 4-vinylcyclohexene epoxide (VCHE, 9 grams) was added with stirring using a magnetic stir bar at ambient temperature. Then Karstedt catalyst (10 microliters of dichloromethane solution) was added. An exothermic reaction ensued. After being stirred overnight (18 hours), the volatiles were removed from the reaction mixture using a rotary evaporator. The residual material remaining in the evaporation flask was a colorless liquid, which was characterized by infrared (IR) and nuclear magnetic resonance (NMR) spectroscopy to be the desired first intermediate product, $M^E(D)_6M^E$, wherein $M^E$ and D are as defined above. The product weighing 23.5 grams represents 82 percent of the theoretical yield. The proton NMR spectrum of the product, shown in FIG. 1 with peak assignments, showed the relative intensity ratio of the peaks due to the epoxy protons, cyclohexyl and adjacent methylene protons, Si—CH$_2$ protons, and Si—CH$_3$ protons to be 4:18:18:44, respectively, as expected by theory.

Figure 2:
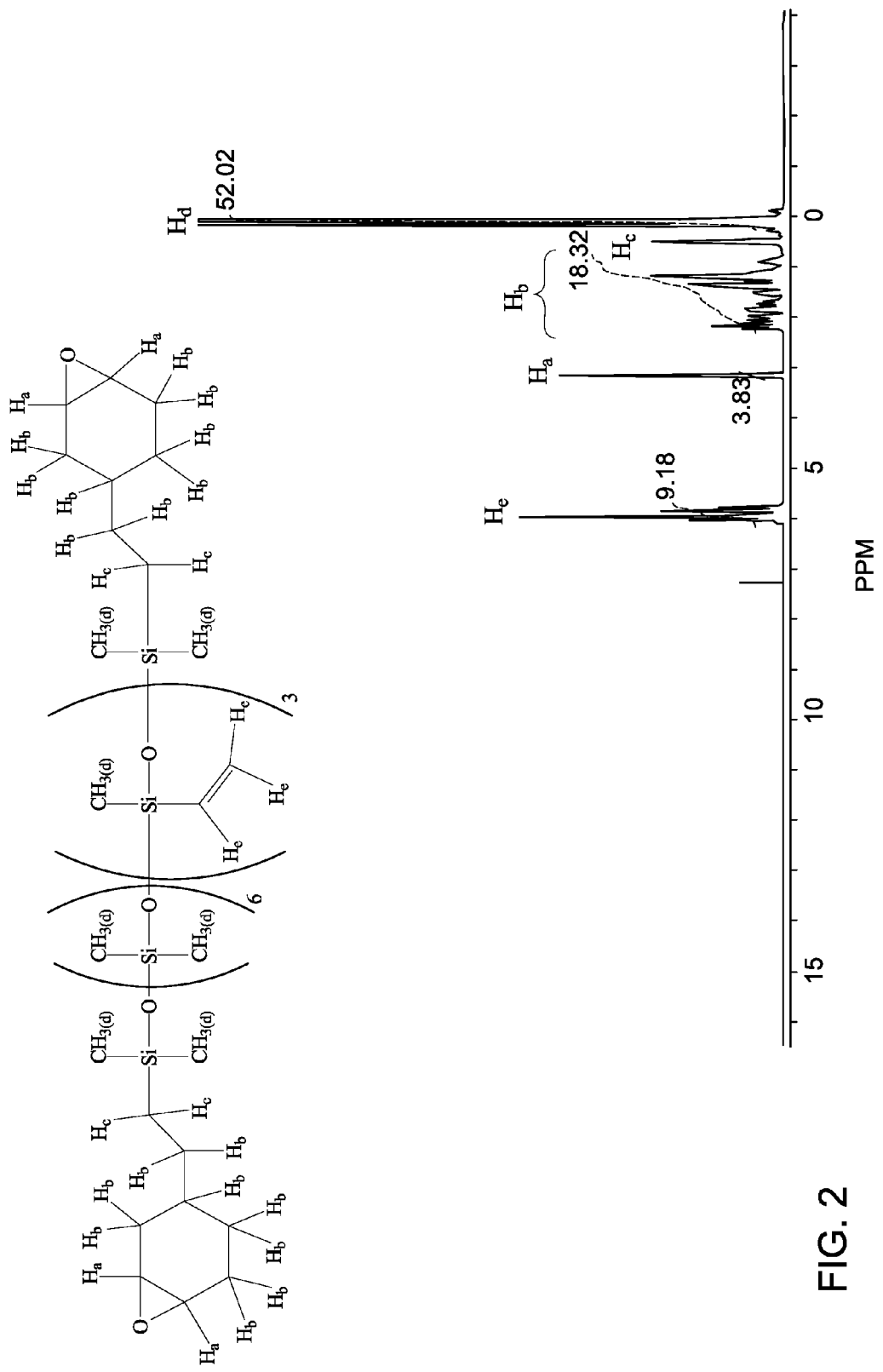
FIG. 2 represents a proton nuclear magnetic resonance spectrum with peak assignments for the second intermediate product $M^E(D)_6(D^{Vi})_3M^E$, described in Example 1.

To a stirred mixture of $M^E(D)_6M^E$ (57.9 grams) and $(D^{Vi})_4$ (18.1 grams), where $D^{Vi}=CH_3(CH=CH_2)SiO_{2/2}$, was added at ambient temperature cesium hydroxide catalyst (10 parts per million relative to the combined weight of $M^E(D)_6M^E$ and $(D^{Vi})_4$. The resulting mixture was heated to a temperature of 130° C. The course of the reaction was monitored by measuring the solids content. After heating for 28 hours, the solids content was found to be constant at 90.5 percent. The volatiles were then removed by vacuum distillation, and the residual material remaining in the reaction flask was characterized by IR and NMR spectroscopy to be the desired second intermediate product, $M^E(D)_6(D^{Vi})_3M^E$. The weight of the isolated product was 68.5 grams (90 percent of theory). The proton NMR spectrum of the product, shown in FIG. 2 with peak assignments, showed the relative intensity ratio of the peaks due to the vinyl protons, epoxy protons, cyclohexyl and adjacent methylene protons, Si—CH$_2$ protons, and Si—CH$_3$ protons to be 9:4:15:18:57, respectively, as expected by theory. Further, the silicon-29 NMR spectrum of the product showed peaks for the $M^E$ silicon, D silicon, and $D^{Vi}$ silicon in a relative ratio of 2:6:3, as expected by theory. The IR spectrum of the product, taken in the attenuated total reflectance mode, showed resonances at 2961, 1598, 1408, 1258, 1018, 793, 633, and 538 reciprocal centimeters (cm$^{-1}$).

Figure 3:
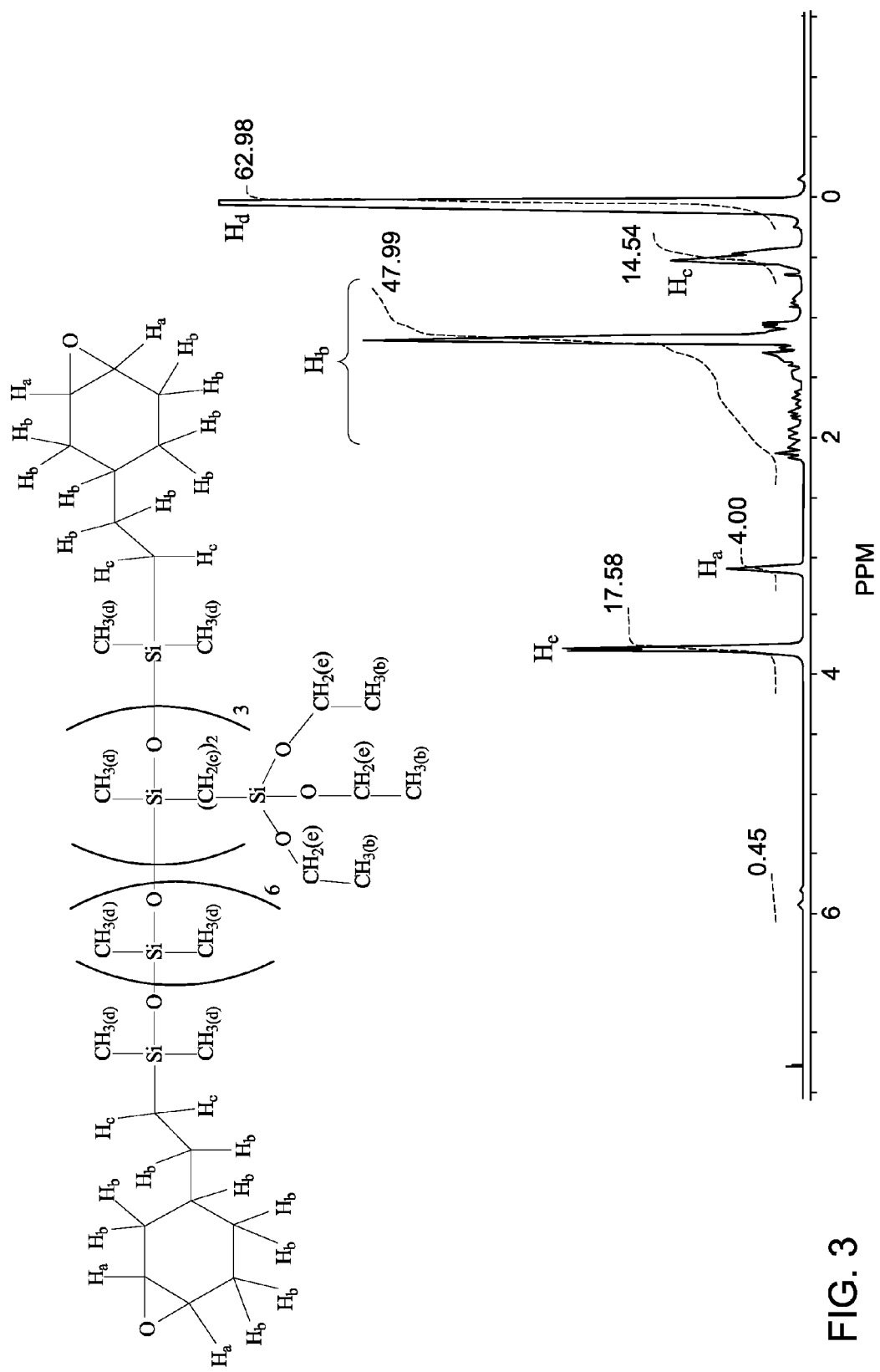
FIG. 3 represents a proton nuclear magnetic resonance spectrum with peak assignments for an exemplary composition, in accordance with an embodiment of the invention.
Figure 4:
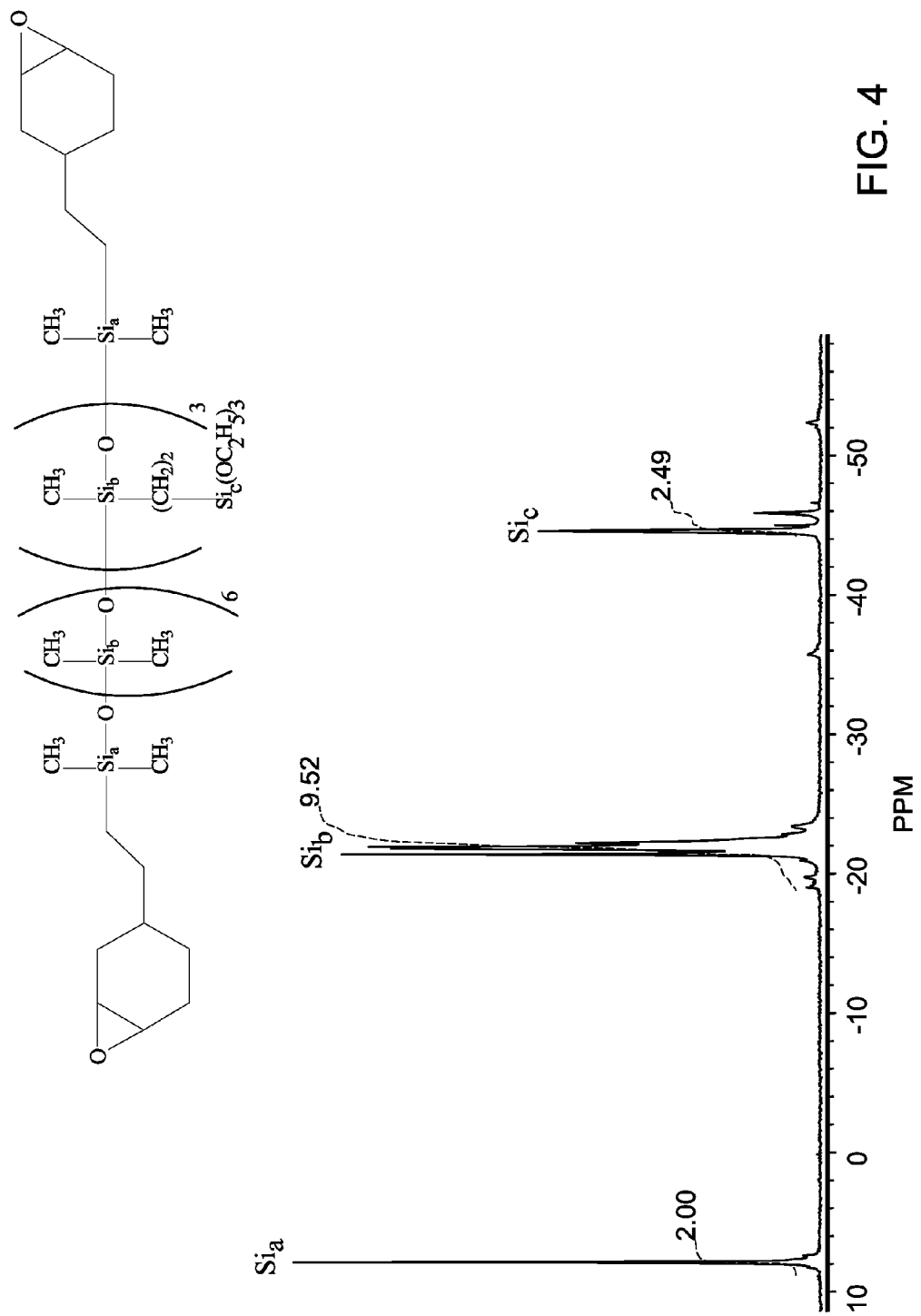
FIG. 4 represents a silicon-29 nuclear magnetic resonance spectrum with peak assignments for the exemplary composition of FIG. 3, in accordance with another embodiment of the invention.

In a 250 milliliter two-necked round-bottomed flask, $M^E(D)_6(D^{Vi})_3M^E$ (23 grams) was taken and treated with triethoxysilane (10.4 grams) at ambient temperature. The stirred mixture was then treated with Karstedt catalyst (10 parts per million with respect to the combined weight of $M^E(D)_6(D^{Vi})_3M^E$ and triethoxysilane and heated to a temperature of 70° C. The course of the reaction was monitored by IR spectroscopy by monitoring the disappearance of the Si—H absorption band. After being heated for 24 hours the Si—H IR absorption band disappeared completely. The volatiles were evaporated from the reaction mixture by vacuum distillation to leave a residual material, which was characterized by IR and NMR spectroscopy to be the desired product, $M^E(D)_6(D^7)_3M^E$. The product was obtained in a yield of 29 grams (87 percent of theory). Proton NMR spectrum shown in FIG. 3 with peak assignments showed the relative intensity ratio of the peaks due to the OCH$_2$ protons, epoxy protons, combination of the cyclohexyl protons, CH$_2$ protons adjacent to the cyclohexyl group, and methyl protons of the ethoxy groups, Si—CH$_2$ protons, and Si—CH$_3$ protons to be 18:4:45:16:57, respectively, which is very close to that expected by theory. Further, the silicon-29 NMR spectrum of the product, shown with peak assignments in FIG. 4, showed peaks for the $M^E$ silicon, D silicon, and $D^{Vi}$ silicon in a relative ratio of 2:6:3, as expected by theory. The IR spectrum of the product, taken in the attenuated total reflectance mode, showed resonances at 2963, 1444, 1390, 1257, 1073, 1016, 750, and 542 reciprocal centimeters (cm$^{-1}$).

Examples 2 and 3 and Control-1. These Examples describe the use of the organosilicone compositions disclosed herein for preparing polymer formulations having reduced gloss. The ingredients used were: (a) bisphenol A Polycarbonate having a weight average molecular weight of about 33,000 to about 35,000; (b) PET (polyethylene terephthalate, having an intrinsic viscosity of about 0.43); (c) MBS (methacrylate-butadiene-styrene copolymer, purchased from Rohm and Haas Company); (d) Pentaerythritol beta-laurylthiopropionate (abbreviated as PLTP); (e) Hindered phenol stabilizer; (f) UVA 234 (a UV stabilizer); (g) PETS (pentaerythritol tetrastearate; (h) Carbon black; and (i) epoxy-capped silicone prepared as described in Example 1. The ingredients were taken in the appropriate amounts as shown in Table 1 and blended and molded into plaques. Then the gloss values were measured for the plaques. The gloss values are shown at the bottom of Table 1.

The data shows that in the case of formulations containing MBS, the formulation represented as Control-1, which does not contain the epoxy-capped silicone has a higher gloss than formulations of Examples 2 and 3, which contain 0.25 weight and 3 weight percent of the epoxy-capped silicone, respectively. Further, it is also evident from Examples 2 and 3 that the when the weight percent of the epoxy-capped organosilicone increases from 0.25 to 3 weight percent, the gloss of the polymer formulation decreases from 96.5 to 87.5.

| Ingredients | Example Number and weight percent of ingredients for Polymer Formulations | | |
|---|---|---|---|
| | Control-1 | Example 2 | Example 3 |
| Polycarbonate | 65.95 | 65.70 | 62.95 |
| PET for F108A | 19.00 | 19.00 | 19.00 |
| MBS | 12.00 | 12.00 | 12.00 |
| PLTP | 0.20 | 0.20 | 0.20 |
| Hindered Phenol stablizer | 0.30 | 0.30 | 0.30 |
| UVA 234 | 0.25 | 0.25 | 0.25 |
| PETS | 0.30 | 0.30 | 0.30 |
| Carbon black | 2.00 | 2.00 | 2.00 |
| Bisepoxy silane | 0 | 0.25 | 3.00 |
| Gloss values for Polymer Formulations | 98.4 | 96.5 | 87.5 |

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for preparing a composition, comprising:

reacting an organosilicon hydride having a structure $(M^1)_a(M^H)_b(D^1)_c(T)_e(Q)_f$ with an epoxyolefin to form a first intermediate product having a structure $(M^1)_a(M^E)_b(D^1)_c(T)_e(Q)_f$; wherein $M^1=R^1R^2R^3SiO_{1/2}$; $M^H=R^4R^5HSiO_{1/2}$; $D^1=R^6R^7SiO_{2/2}$; $T=R^{10}SiO_{3/2}$; $Q=SiO_{4/2}$; and $M^E=R^4R^5R^ESiO_{1/2}$; wherein $R^1$, $R^2$, $R^3$, $R^4$, $R^5$, $R^6$, $R^7$, and $R^{10}$ are independently monovalent hydrocarbon radicals; each $R^E$ is independently a monovalent hydrocarbon radical containing an epoxy group; and a, b, c, e, and f are stoichiometric subscripts that are zero or positive subject to the following limitations: b has a value such that $0<b\leq2$; and when (a+c+e+f) is equal to zero, b is equal to 2;

reacting said first intermediate product with a cyclic siloxane having a structure $(D^6)$, to form a second intermediate product having a structure $(M^1)_a(M^E)_b(D^1)_c(D^6)_o(T)_e(Q)_f$; wherein $D^6$ is $R^8R^{28}SiO_{2/2}$, wherein $R^8$ is a monovalent hydrocarbon radical, $R^{28}$ is a monovalent alkenyl group; a, b, c, e, f, n, and o are stoichiometric subscripts that are zero or positive subject to the following limitations: n is greater than or equal to 3; o is at least 1; b has a value of 2; and when (a+c+e+f) is equal to zero, (b+o) is greater than or equal to 3; and reacting said second intermediate product with an (alkoxy) hydrosilane to form said composition having a structure $(M^1)_a(M^E)_b(D^1)_c(D^2)_d(T)_e(Q)_f$; wherein $M^1=R^1R^2R^3SiO_{1/2}$; $M^E=R^4R^5R^ESiO_{1/2}$; $D^1=R^6R^7SiO_{2/2}$; $D^2=R^8R^9SiO_{2/2}$; $T=R^{10}SiO_{3/2}$; and $Q=SiO_{4/2}$; wherein each $R^E$ is independently a monovalent hydrocarbon radical containing an epoxy group; $R^9$ comprises a pendant functional organosilicon group comprising a structure $-L^1-Si(R^{11})_g(OR^{12})_{3-g}$ or $L^2(D^3)_h-L^3-Si(R^{13})_{g'}(OR^{14})_{3-g'}$, wherein $L^1$, $L^2$, and $L^3$ are independently divalent linking groups; g and g' independently have a value from 0 to 2; $D^3=R^{18}R^{19}SiO_{2/2}$; wherein $R^1$, $R^2$, $R^3$, $R^4$, $R^5$, $R^6$, $R^7$, $R^8$, $R^{10}$, $R^{11}$, $R^{12}$, $R^{13}$, $R^{14}$, $R^{15}$, $R^{16}$, $R^{17}$, $R^{18}$, and $R^{19}$ are independently monovalent hydrocarbon radicals;

wherein a, b, c, d, e, f, h, and i are stoichiometric subscripts that are zero or positive subject to the following limitations: b has a value of 2; d is greater than or equal to 1; when (a+c+e+f) is equal to zero, (b+d) is greater than or equal to 3; and when i=0, h is at least 1.

2. The method of claim 1, wherein said epoxyolefin has a structure:

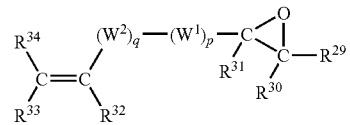

wherein $R^{29}$, $R^{30}$, $R^{31}$, $R^{32}$, $R^{33}$, and $R^{34}$ are independently selected from the group consisting of hydrogen atom and monovalent hydrocarbon radicals having from one to sixty carbon atoms, $W^1$ is a divalent or a trivalent hydrocarbon radical having from one to sixty carbon atoms, $W^2$ is a divalent hydrocarbon radical having from one to sixty carbon atoms, and the subscripts p and q are independently zero or one subject to the limitation that when $W^1$ is trivalent, one of $R^{29}$ or $R^{30}$ is a hydrogen atom.

3. The method of claim 2, wherein said epoxyolefin is selected from the group consisting of limonene oxide, 1,2-epoxy-7-octene, 1,2-epoxy-9-decene, 1,2-epoxy-4-vinylcyclohexane, 1,2-epoxy-5-hexene, 1,2-epoxy-9-decene, 3,4-epoxy-1-butene, allyl glycidyl ether, 1,2-epoxy-7-octene, 2,3-epoxy-5,6-norbornene, 2-(4-allyloxyphenyl)-2-(4-glycidyloxyphenyl)propane, and mixtures thereof.

4. The method of claim 3, wherein $R^8$ is selected from the group consisting of methyl, ethyl, sec-butyl, tert-butyl, octyl, decyl, dodecyl, cetyl, butoxy, hydroxypropyl, 2,5,8-trioxadecyl, triacontyl, and 3,3,3-trifluoropropyl; $R^{28}$ is selected from the group consisting of 1-ethenyl, 1-propenyl, 1-butenyl, 1-pentenyl, and styrenyl; and n has a value of 3-6.

5. The method of claim 4, wherein $R^8$ is methyl, $R^{28}$ is 1-ethenyl, and n is 4.

6. The method of claim 1, wherein e and f are zero, a is at least 1 with the limitation that (a+b)=2; and c has a value from 0-500.

7. The method of claim 1, wherein said (alkoxy)hydrosilane comprises triethoxysilane.

* * * * *